United States Patent
Lecompte

(10) Patent No.: US 9,282,716 B2
(45) Date of Patent: Mar. 15, 2016

(54) WITLOOF CHICORY BOBINE

(71) Applicant: Vilmorin S.A., La Menitre (FR)

(72) Inventor: Alain Lecompte, La Menitre (FR)

(73) Assignee: VILMORIN S.A., La Menitre (FR)

( * ) Notice: Subject to any disclaimer, the term of this patent is extended or adjusted under 35 U.S.C. 154(b) by 118 days.

(21) Appl. No.: 14/226,326

(22) Filed: Mar. 26, 2014

(65) Prior Publication Data

US 2015/0272075 A1 Oct. 1, 2015

(51) Int. Cl.
*A01H 5/12* (2006.01)
*C12N 5/04* (2006.01)
*A01H 4/00* (2006.01)

(52) U.S. Cl.
CPC .. *A01H 5/12* (2013.01); *A01H 4/00* (2013.01); *C12N 5/04* (2013.01)

(58) Field of Classification Search
CPC ............... A01H 5/12; A01H 4/00; C12N 5/04
USPC ........................................................ 800/265
See application file for complete search history.

(56) References Cited

U.S. PATENT DOCUMENTS 6,803,497 B1 10/2004 Delesalle et al.
2006/0260001 A1* 11/2006 Lecompte ................ A01H 5/12
800/278

OTHER PUBLICATIONS

U.S. Appl. No. 10/554,282, filed Nov. 16, 2006, Lecompte A.
Charles M. Rick, Proceedings of the American Society for Horticultural Science, vol. 61, 459-466, 1953.
Sidikou-Seyni et al., Plant Cell Tissue and organ Culture, vol. 29, 83-91, 1992.
Tan et al., HortScience, 25(11), 1396-1398, 1990.
Van Stallen et al., Plant Cell Tissue and organ Culture, vol. 55, 125-131, 1999.
Blervacq et al., Protoplasma, vol. 186, 3-4, 163-168, 1995.
Papetti Adele et al., Journal of Agricultural and food chemistry, vol. 50, No. 16, Jul. 31, 2002, pp. 4696-4704.
Helleboid Stephane et al., Journal of experimental botany, vol. 51, No. 348, Jul. 2000, pp. 1189-1200.
Helleboid Stephane et al., Plant A (Heidelberg), vol. 196, No. 3, 1995, pp. 571-576.
Castano et al., Scientia Horticulture (1997), vol. 72, pp. 1-9.

* cited by examiner

*Primary Examiner* — Li Zheng
(74) *Attorney, Agent, or Firm* — Cooley LLP

(57) ABSTRACT

A novel witloof chicory cultivar, designated 'BOBINE', is disclosed. The invention relates to the seeds of witloof chicory cultivar 'BOBINE', to the plants of witloof chicory cultivar 'BOBINE' and to methods for producing a witloof chicory plant by crossing the cultivar 'BOBINE' with itself or another witloof chicory line. The invention further relates to methods for producing other witloof chicory lines derived from the cultivar 'BOBINE'.

12 Claims, 3 Drawing Sheets

'BOBINE' chicon

WITLOOF CHICORY BOBINE

FIELD OF THE INVENTION

The present invention relates to a new and distinctive chicory cultivar designated 'BOBINE' and classified as a witloof chicory (*Cichorium intybus* L)

BACKGROUND OF THE INVENTION

Plants from *Cichorium intybus* L species adapted to forcing culture, also called endives or witloof chicory, are widely grown throughout Europe and temperate areas in Asia. It is a very branchy plant, with stiff branches being spaced apart from one another. The lower leaves are usually divided, with lobes or segments arranged on both sides, spaced apart and often inverted, with an end lobe; the top leaves are entire, encompassing the stem with their base, and the higher leaves are reduced to relatively small bracts. The root parenchymal cells produce holosides (starch, inulin, etc) from substances originating from green organs where they have been synthesized. During the growth phase, roots constantly bulge out as a result of hyperplasia of their parenchymae, with holosides accumulating therein, so as to form tuberous roots.

The ability of the *Cichorium intybus* L species, and more specifically of some varieties of such a species, such as the Witloof type varieties, to produce tuberous roots makes such plants adapted to being grown in the dark through forcing culture. The cultivation, for a 21 day forcing, comprises growing endives in tubs containing a nutrient solution brought to a temperature from about 18° C. to about 21° C. and an air temperature of about 1° C. to 3° C. lower than the nutrient solution temperature. Endives are grown through forcing in the dark so as to cause the leaves to wilt in order to produce essentially white mature plants with the outer edge of the leaves only having a slight yellow color.

Producing endives through forcing traditionally occurs at a large scale in rooms where tubs are stacked wherein endive roots are immersed in a nutrient solution, under dark conditions, under solution and room temperature conditions, and under accurately controlled hygrometry conditions. Thus, forcing cultivation of endive requires significant financial investments both in equipment and labor in order to achieve the various respective steps of sowing, root harvesting, and their forcing in a cultivation room, in order to produce endives at a large scale.

Cultivating endives through forcing is intended to produce chicories that will be marketed. Chicories are essentially made of leaves wilting in the dark, originating from the root neck. Forcing cycles are subjected to highly accurate and planned cultivation conditions, cycles and schedules so as to optimize the production costs.

In order to make available for the consumers a novel and varied range of plants derived from endive, able to be marketed at reasonable costs, it is required that the novel plants should be adapted to the production conditions being traditionally used for the endive. Indeed, new industrial investments that should be specifically adapted to the production of new plants of the *Cichorium* species would not be economically compatible with the market. Any new variety intended to be produced through forcing should, consequently, be able to integrate in the production system already developed for the endive.

The witloof chicory type *Cichorium intybus* L is an important and valuable vegetable crop. Thus, a continuing goal of witloof chicory plant breeders is to develop stable, high yielding witloof chicory cultivars that are agronomically sound. The reasons for this goal are obviously to maximize the amount of yield produced. To accomplish this goal, the witloof chicory breeder must select and develop witloof chicory plants that have traits that result in superior cultivars.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there is provided a novel witloof chicory cultivar designated 'BOBINE'. This invention thus relates to the seeds of witloof chicory cultivar 'BOBINE', to the plants or part(s) thereof of witloof chicory cultivar 'BOBINE', to plants or part(s) thereof consisting essentially of the phenotypic and morphological characteristics of witloof chicory cultivar 'BOBINE', and/or having all the phenotypic and morphological characteristics of witloof chicory cultivar 'BOBINE', and/or having the phenotypic and morphological characteristics of witloof chicory cultivar 'BOBINE' listed in Table 1 including but not limited to as determined at the 5% significance level when grown in the same environmental conditions. The invention also relates to variants, mutants and trivial modifications of the seed or plant of witloof chicory cultivar 'BOBINE'. Plant parts of the witloof chicory cultivar of the present invention are also provided such as, i.e., pollen obtained from the plant cultivar and an ovule obtained from the plant cultivar.

The plants and seeds of the present invention include those that may be of an essentially derived variety as defined in section 41(3) of the Plant Variety Protection Act, i.e., a variety that:

(i) is predominantly derived from witloof chicory cultivar 'BOBINE' or from a variety that is predominantly derived from witloof chicory cultivar 'BOBINE', while retaining the expression of the essential characteristics that result from the genotype or combination of genotypes of witloof chicory cultivar 'BOBINE';

(ii) is clearly distinguishable from witloof chicory cultivar 'BOBINE'; and (iii) except for differences that result from the act of derivation, conforms to the initial variety in the expression of the essential characteristics that result from the genotype or combination of genotypes of the initial variety.

In another aspect, the present invention provides regenerable cells for use in tissue culture of witloof chicory cultivar 'BOBINE'. The tissue culture will be capable of regenerating plants consisting essentially of the phenotypic and morphological characteristics of witloof chicory cultivar 'BOBINE', and/or having all the phenotypic and morphological characteristics witloof chicory cultivar 'BOBINE', and/or having the phenotypic and morphological characteristics of witloof chicory cultivar 'BOBINE'. The cells of such tissue culture will be embryos, meristematic cells, seeds, callus, pollen, leaves, anthers, pistils, roots, root tips, flowers and stems. Protoplasts produced from such tissue culture are also included in the present invention. The witloof chicory shoots, roots and whole plants regenerated from the tissue culture are also part of the invention.

Also included in the invention are methods for producing a witloof chicory plant produced by crossing witloof chicory cultivar 'BOBINE' with itself or another witloof chicory cultivar. When crossed with itself, i.e., when crossed with another witloof chicory cultivar 'BOBINE' plant or self-pollinated, witloof chicory cultivar 'BOBINE' will be conserved (e.g., as an inbred). When crossed with another, different witloof chicory plant, an $F_1$ hybrid seed is produced. $F_1$ hybrid seeds and plants produced by growing said hybrid seeds are included in the present invention. A method for producing an $F_1$ hybrid witloof chicory seed comprising crossing a witloof chicory cultivar 'BOBINE' plant with a different witloof chicory plant and harvesting the resultant hybrid witloof chicory seed are also part of the invention. The hybrid witloof chicory seed produced by the method comprising crossing a witloof chicory cultivar 'BOBINE' plant with a different witloof chicory plant and harvesting the resultant hybrid witoof chicory seed, are included in the invention, as are the hybrid witloof chicory plant or part(s) thereof, and seeds produced by growing said hybrid witloof chicory seed.

In another aspect, the present invention provides for methods of introducing one or more desired trait(s) into witloof chicory cultivar 'BOBINE' and plants obtained from such methods. The desired trait(s) may be, but not exclusively, a single gene, preferably a dominant but also a recessive allele. The transferred gene or genes will confer such traits as male sterility, herbicide resistance, insect resistance, resistance to bacterial, fungal, or viral disease, increased leaf number, improved shelf-life, delayed senescence and tolerance to water stress or heat stress. The gene or genes may be naturally occurring gene(s). The method for introducing the desired trait(s) may be a backcrossing process making use of a series of backcrosses to witloof chicory cultivar 'BOBINE' during which the desired trait(s) is maintained by selection.

The backcross breeding process comprises the following steps: (a) crossing witloof chicory cultivar 'BOBINE' plants with plants of another cultivar that comprise the desired trait(s); (b) selecting the $F_1$ progeny plants that have the desired trait(s); (c) crossing the selected $F_1$ progeny plants with witloof chicory cultivar 'BOBINE' plants to produce backcross progeny plants; (d) selecting for backcross progeny plants that have the desired trait(s) and physiological and morphological characteristics of witloof chicory cultivar 'BOBINE' to produce selected backcross progeny plants; and (e) repeating steps (c) and (d) one, two, three, four, five six, seven, eight, nine, or more times in succession to produce selected, second, third, fourth, fifth, sixth, seventh, eighth, ninth, or higher backcross progeny plants that consist essentially of the phenotypic and morphological characteristics of witloof chicory cultivar 'BOBINE', and/or have all the phenotypic and morphological characteristics of witloof chicory cultivar 'BOBINE', and/or have the desired trait(s) and the physiological and morphological characteristics of witloof chicory cultivar 'BOBINE' as determined in Table 1, including but not limited to a 5% significance level when grown in the same environmental conditions. The witloof chicory plants produced by the methods are also part of the invention. Backcrossing breeding methods, well-known for one skilled in the art of plant breeding, will be further developed in subsequent parts of the specification.

In one embodiment, the present invention provides methods for increasing and producing witloof chicory cultivar 'BOBINE' seed, whether by crossing a first parent witloof chicory cultivar plant with a second parent witloof chicory cultivar plant and harvesting the resultant witloof chicory seed, wherein both said first and second parent witloof chicory cultivar plant are the witloof chicory cultivar 'BOBINE' or by planting a witloof chicory seed of the witloof chicory cultivar 'BOBINE', growing a witloof chicory cultivar 'BOBINE' plant from said seed, controlling a self pollination of the plant where the pollen produced by a grown witloof chicory cultivar 'BOBINE' plant pollinates the ovules produced by the very same witloof chicory cultivar 'BOBINE' grown plant, and harvesting the resultant seed.

The invention further provides methods for developing cultivars in a witloof chicory breeding program using plant breeding techniques including recurrent selection, backcrossing, pedigree breeding, molecular markers (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc.) enhanced selection, genetic marker enhanced selection, and transformation. Seeds, witloof chicory plants, and part(s) thereof produced by such breeding methods are also part of the invention.

In some embodiments, the present invention teaches a seed of a witloof chicory cultivar designated 'BOBINE', wherein a representative sample of seed of said cultivar has been deposited under NCIMB No. 42468.

In some embodiments, the present invention also teaches a witloof chicory plant, or a part thereof, produced by growing a seed of said cultivar that has been deposited under NCIMB No. 42468.

In some embodiments, the present invention teaches a witloof chicory plant, or a part thereof, having all the physiological and morphological characteristics of the witloof chicory cultivar 'BOBINE' listed in Table 1.

In some embodiments, the present invention teaches a witloof chicory plant, or a part thereof, having the physiological and morphological characteristics of a witloof chicory cultivar 'BOBINE', wherein a representative sample of seed of said cultivar has been deposited under NCIMB No. 42468.

In some embodiments, the present invention teaches a tissue culture of regenerable cells produced from the 'BOBINE' plant of the present invention, wherein said cells of the tissue culture are produced from a plant part selected from the group consisting of embryos, meristematic cells, leaves, pollen, root, root tips, stems, anther, pistils, flowers, and seeds.

In some embodiments, the present invention teaches a witloof chicory plant regenerated from the tissue culture the 'BOBINE' plant of the present invention, said plant having the morphological and physiological characteristics of witloof chicory cultivar 'BOBINE', wherein a representative sample of seed has been deposited under NCIMB No. 42468.

In some embodiments, the present invention teaches a method for producing a witloof chicory seed comprising crossing a first parent witloofchicory plant with a second parent witloof chicory plant and harvesting the resultant hybrid witloof chicory seed, wherein said first parent witloof chicory plant or second parent witloof chicory plant is the 'BOBINE' witloof chicory plant of the present invention.

In some embodiments, the present invention teaches a hybrid witloof chicory seed produced by the plant crossing methods of the present invention.

In some embodiments, the present invention teaches a method of introducing a desired trait into a witloof chicory cultivar 'BOBINE' comprising: (a) crossing a witloofchicory cultivar 'BOBINE' plant grown from witloof chicory cultivar 'BOBINE' seed, wherein a representative sample of seed has been deposited under NCIMB No. 42468 with another witloof chicory plant that comprises a desired trait to produce $F_1$ progeny plants, wherein the desired trait is selected from the group consisting of insect resistance, disease resistance, water stress tolerance, heat stress tolerance, improved shelf life, delayed shelf life, increased leaf number and male sterility; (b) selecting one or more progeny plants that have the desired trait to produce selected progeny plants; (c) crossing the selected progeny plants with the witloof chicory cultivar 'BOBINE' plants to produce backcross progeny plants; (d) selecting for backcross progeny plants that have the desired trait and physiological and morphological characteristics of witloof chicory cultivar 'BOBINE' listed in Table 1 to produce selected backcross progeny plants; and (e) repeating steps (c) and (d) three or more times in succession to produce selected fourth or higher backcross progeny plants that comprise the desired trait and the physiological and morphological characteristics of witloof chicory cultivar 'BOBINE' listed in Table 1.

In some embodiments, the present invention teaches a witloof chicory plant produced by the breeding methods of the present invention, wherein the plant has the desired trait and the physiological and morphological characteristics of witloof chicory cultivar 'BOBINE' listed in Table 1.

In some embodiments, the present invention teaches a method for producing witloof chicory cultivar 'BOBINE' seed comprising crossing a first parent witloof chicory plant with a second parent witloof chicory plant and harvesting the resultant witloof chicory seed, wherein both said first and second witloof chicory plants are the 'BOBINE' witloof chicory plant of the present invention.

In some embodiments, the present invention teaches a witloof chicory head, produced by forcing the 'BOBINE" plant of the present invention.

In addition to the exemplary aspects and embodiments described above, further aspects and embodiments will become apparent by study of the following descriptions.

DETAILED DESCRIPTION OF THE INVENTION

Definitions

Figure 1:
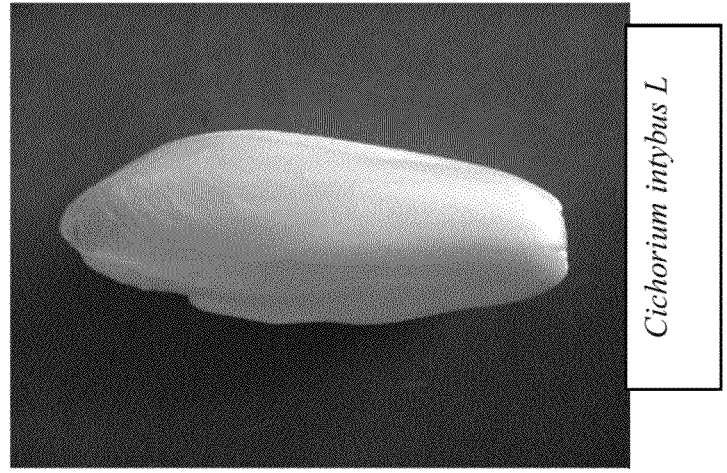
FIG. 1 is a diagram representing the cross between *Cichorium endivia* L and *Cichorium intybus* L performed as described in US patent publication US 2006/0260001 to produce parental lines 17.1 and 119729.07 of the present invention.
Figure 1:
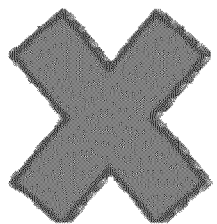
Figure 1:
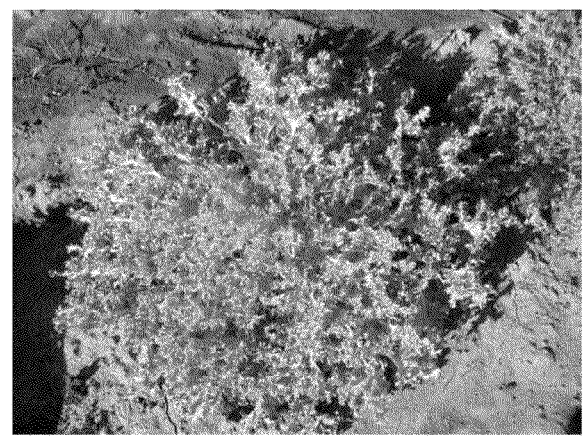

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Essentially all the physiological and morphological characteristics. A plant having essentially all the physiological and morphological characteristics means a plant having the physiological and morphological characteristics, except for the characteristics derived from the converted gene.

GPI phenotype: A plant having a GPI phenotype according to the invention is a plant having from 20 to 35 leaves per root at the completion of the forcing, plant having no secondary axis, a plant having deep indentations of the limb up to the leaf basis, a plant having a ratio depth of the indentation/length of the indentation tip to the leaf axis ranging from 0.60 to 0.85, a plant whereas the edge of the indentations can comprise secondary serrations, a plant where the color of the nervures is white or red, a plant where the color of the limb is yellow or red.

Immunity to disease(s) and or insect(s). A witloof plant which is not subject to attack or infection by specific disease(s) and or insect(s) is considered immune.

Intermediate resistance to disease(s) and or insect(s). A witloof plant that restricts the growth and development of specific disease(s) and or insect(s), but may exhibit a greater range of symptoms or damage compared to resistant plants. Intermediate resistant plants will usually show less severe symptoms or damage than susceptible plant varieties when grown under similar environmental conditions and/or specific disease(s) and or insect(s) pressure, but may have heavy damage under heavy pressure. Intermediate resistant witloof plants are not immune to the disease(s) and or insect(s).

Media NF: The qualitative and quantitative composition of the culture media NF is as follow for one liter: MS macro elements (×10): 100 ml; MS microelements (×1000): 1 ml; Inositol-free Gamborg vitamins (×1000): 1 ml; NaFeEDTA (×100): 10 ml; Casein hydrolysate: 1 g; Sucrose: 40 g; Inositol: 50 mg; BAP (dissolve in NaOH 1N): 0.2 mg; pH=5.6; Agar: 10 g.

Media M4: The qualitative and quantitative composition of the culture media M4 is as follow for one liter: MS macro elements (×10): 100 nil; MS microelements (×1000): 1 ml; Inositol-free MS vitamins (×1000): 1 ml; NaFeEDTA (×100): 10 ml; Sucrose: 30 g; Inositol: 100 mg; AIA (dissolve in 95° pure alcohol): 0.2 mg; pH=5.8; Agar: 8 g.

Plant: as used herein, the term plant may designate the plant as cultivated in the field, or indoor facility, with a horizontal foliage attitude or the plant as cultivated in forcing conditions with an erected head.

Plant adaptability. A plant having good plant adaptability means a plant that will perform well in different growing conditions and seasons.

Plant cell. As used herein, the term "plant cell" includes plant cells whether isolated, in tissue culture, or incorporated in a plant or plant part.

Plant part. As used herein, the term "plant part" includes any part of the plant including but not limited to leaves, stems, roots, seed, embryos, pollen, ovules, flowers, root tips, anthers, tissue, cells, tuberous roots, head and the like.

Regeneration. Regeneration refers to the development of a plant from tissue culture.

Resistance to disease(s) and or insect(s). A witloof plant that restricts the growth and development of specific disease(s) and or insect(s) under normal disease(s) and or insect(s) attack pressure when compared to susceptible plants. These witloof plants can exhibit some symptoms or damage under heavy disease(s) and or insect(s) pressure. Resistant witloof chicory plants are not immune to the disease(s) and or insect(s).

Single gene converted (conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

Susceptible to disease(s) and or insect(s). A witloof plant that is susceptible to disease(s) and or insect(s) is defined as a witloof plant that has the inability to restrict the growth and development of specific disease(s) and or insect(s). Plants that are susceptible will show damage when infected and are more likely to have heavy damage under moderate levels of specific disease(s) and or insect(s).

Breeding New Varieties

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety an improved combination of desirable traits from the parental germplasm.

Choice of breeding or selection methods depends on the mode of plant reproduction, the heritability of the trait(s) being improved, and the type of cultivar used commercially (e.g., $F_1$ hybrid cultivar, pure line cultivar, etc.). For highly heritable traits, a choice of superior individual plants evaluated at a single location may be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

The complexity of inheritance influences choice of the breeding method. Backcross breeding is used to transfer one or a few favorable genes for a highly heritable trait into a desirable cultivar. This approach has been used extensively for breeding disease-resistant cultivars. Nevertheless, it is also suitable for the adjustment and selection of morphological character, color characteristics and simply inherited quantitative characters. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars. Those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and/or to a widely grown standard cultivar. If a single observation is inconclusive, replicated observations provide a better estimate of its genetic worth.

The goal of witloof chicory plant breeding is to develop new, unique and superior witloof chicory cultivars. The breeder initially selects and crosses two or more parental lines, followed by repeated selfing and selection, producing many new genetic combinations. Another method used to develop new and unique witloof chicory cultivar occurs when the witloof chicory breeder selects and crosses parental varieties followed by haploid induction and chromosome doubling that result in the development of dihaploïd cultivars. The breeder can theoretically generate billions of different genetic combinations via crossing, selling and mutations and the same is true for the utilization of the dihaploïd breeding method.

Each year, the plant breeder selects the germplasm to advance to the next generation. This germplasm is grown under unique and different geographical, climatic and soil conditions and further selections are then made during and at the end of the growing season. The cultivars that are developed are unpredictable. This unpredictability is because the breeder's selection occurs in unique environments with no control at the DNA level (using conventional breeding procedures or dihaploïd breeding procedures), and with millions of different possible genetic combinations being generated. A breeder of ordinary skill in the art cannot predict the final resulting lines he develops, except possibly in a very gross and general fashion. This unpredictability results in the expenditure of large amounts of research monies to develop superior new witloof chicory cultivars.

The development of new witloof chicory cultivars requires the development and selection of witloof chicory varieties, the crossing of these varieties and the evaluation of the crosses.

Pedigree breeding and recurrent selection breeding methods are used to develop cultivars from breeding populations. Breeding programs combine desirable traits from two or more cultivars or various broad-based sources into breeding pools from which cultivars of desired phenotypes are developed by selfing and selection or through the dihaploïd breeding method.

Pedigree breeding is used commonly for the improvement of self-pollinating crops or inbred lines of cross-pollinating crops. Two parents that possess favorable, complementary traits are crossed to produce an $F_1$. An $F_2$ population is produced by selfing one or several $F_1$s or by intercrossing two $F_1$s (sib mating). The dihaploïd breeding method could also be used. Selection of the best individuals may begin in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987; Principles of Crop Development, Macmillan Publishing Co.; N. F. Jensen. 1988. Plant Breeding Methodology, John Wiley & Sons).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

This invention also is directed to methods for producing a witloof chicory by crossing a first parent witloof chicory plant with a second parent witloof chicory plant wherein either the first or second parent witloof chicory plant is a witloof chicory plant of the cultivar 'BOBINE'. Further, both first and second parent witloof chicory plants can come from cultivar 'BOBINE'. When self pollinated, or crossed with another witloof chicory cultivar 'BOBINE' plant, the witloof chicory cultivar 'BOBINE' will be stable, while when crossed with another, different witloof chicory cultivar plant, an $F_1$ hybrid seed is produced. Such methods of hybridization and self-pollination of the witloof chicory are well known to those skilled in the art of witloof chicory breeding. See, for example, F. A. Bliss, 1980, Common Bean, In Hybridization of Crop Plants, Fehr and Hadley, eds., Chapter 17: 273-284, American Society of Agronomy and Crop Science Society of America, Publishers.

Still further, this invention also is directed to methods for producing an 'BOBINE'-derived witloof chicory plant by crossing cultivar 'BOBINE' with a second witloof chicory plant and growing the progeny seed, and repeating the crossing and growing steps with the cultivar 'BOBINE'-derived plant from 0 to 7 times. Thus, any such methods using the cultivar 'BOBINE' are part of this invention: selfing, backcrosses, hybrid production, crosses to populations, and the like. All plants produced using cultivar 'BOBINE' as a parent are within the scope of this invention, including plants derived from cultivar 'BOBINE'. Advantageously, the cultivar is used in crosses with other, different, cultivars to produce first generation ($F_1$) witloof chicory seeds and plants with superior characteristics.

As used herein, the term "plant" includes plant cells, plant protoplasts, plant cell tissue cultures from which witloof chicory plants can be regenerated, plant calli, plant clumps and plant cells that are intact in plants or parts of plants, such as embryos, pollen, ovules, flowers, seeds, stems, roots, anthers, pistils, root tips, leaves, and the like.

As is well known in the art, tissue culture of witloof chicory can be used for the in vitro regeneration of a witloof chicory plant. Tissue culture of various tissues of witloof chicory and regeneration of plants there from is well known and widely published. For example, reference may be had to Margara J, 1989, Bases de la multiplication végétative, INRA ed. It is clear from the literature that the state of the art is such that these methods of obtaining plants are routinely used and have a very high rate of success. Thus, another aspect of this invention is to provide cells which upon growth and differentiation produce witloof chicory plants having the physiological and morphological characteristics of witloof chicory cultivar 'BOBINE'.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Backcrossing

When the term witloof chicory plant, cultivar or witloof chicory line are used in the context of the present invention, this also includes cultivars where one or more desired traits has been introduced through backcrossing methods. Backcrossing methods can be used with the present invention to improve or introduce a characteristic into the line. The term "backcrossing" as used herein refers to the repeated crossing of a hybrid progeny back to the recurrent parent, i.e., backcrossing one, two, three, four, five, six, seven, eight, nine, or more times to the recurrent parent. The parental witloof chicory plant which contributes the gene for the desired characteristic is termed the nonrecurrent or donor parent. This terminology refers to the fact that the nonrecurrent parent is used one time in the backcross protocol and therefore does not recur. The parental witloof chicory plant to which the gene or genes from the nonrecurrent parent are transferred is known as the recurrent parent as it is used for several rounds in the backcrossing protocol.

In a typical backcross protocol, the original cultivar of interest (recurrent parent) is crossed to a second line (nonrecurrent parent) that carries the gene or genes of interest to be transferred. The resulting progeny from this cross are then crossed again to the recurrent parent and the process is repeated until a garden witloof chicory plant is obtained wherein essentially all of the desired morphological and physiological characteristics of the recurrent parent are recovered in the converted plant, generally determined at a 5% significance level when grown in the same environmental condition, in addition to the gene or genes transferred from the nonrecurrent parent. It has to be noted that some, one, two, three, or more, self-pollination and growing of population might be included between two successive backcrosses. Indeed, an appropriate selection in the population produced by the self-pollination, i.e., selection for the desired trait and physiological and morphological characteristics of the recurrent parent might be equivalent to one, two or even three, additional backcrosses in a continuous series without rigorous selection, saving time, money and effort to the breeder. A non limiting example of such a protocol would be the following: (a) the first generation $F_1$ produced by the cross of the recurrent parent A by the donor parent B is backcrossed to parent A; (b) selection is practiced for the plants having the desired trait of parent B; (c) selected plants are self-pollinated to produce a population of plants where selection is practiced for the plants having the desired trait of parent B and the physiological and morphological characteristics of parent A; (d) the selected plants are backcrossed one, two, three, four, five, six, seven, eight, nine, or more times to parent A to produce selected backcross progeny plants comprising the desired trait of parent B and the physiological and morphological characteristics of parent A. Step (c) may or may not be repeated and included between the backcrosses of step (d).

The selection of a suitable recurrent parent is an important step for a successful backcrossing procedure. The goal of a backcross protocol is to alter or substitute a single trait or characteristic in the original line. To accomplish this, a gene or genes of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross; one of the major purposes is to add some commercially desirable, agronomical important trait to the plant. The exact backcrossing protocol will depend on the characteristic or trait being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important than the identification of the character(s) in the segregating population. In this instance it may then be necessary to introduce a test of the progeny to determine if the desired characteristic(s) has been successfully transferred. Such tests encompass visual inspection, simple crossing but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele requires selfing the progeny to determine which plant carries the recessive allele(s).

Many single gene traits have been identified that are not regularly selected for in the development of a new line but that can be improved by backcrossing techniques. Single gene traits may or may not be transgenic. Examples of these traits include, but are not limited to, herbicide resistance (such as bar or pat genes), resistance for bacterial, fungal, or viral disease (such as gene I used for BCMV resistance), insect resistance, enhanced nutritional quality (such as 2s albumin gene), industrial usage, agronomic qualities (such as the "persistent green gene"), yield stability, and yield enhancement. These genes are generally inherited through the nucleus. Some other single gene traits are described in U.S. Pat. Nos. 5,777,196, 5,948,957, and 5,969,212, the disclosures of which are specifically hereby incorporated by reference.

In 1981 the backcross method of breeding accounted for 17% of the total breeding effort for inbred corn line development in the United States, according to, Hallauer, A. R., et al., "Corn Breeding." Corn and Corn Improvement, No. 18, pp. 463-481 (1988).

The backcross breeding method provides a precise way of improving varieties that excel in a large number of attributes but are deficient in a few characteristics. (Page 150 of the Pr. R. W. Allard's 1960 book, *Principles of Plant Breeding*, published by John Wiley & Sons, Inc.) The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a variety with exactly the adaptation, yielding ability, and quality characteristics of the recurrent parent but superior to that parent in the particular characteristic(s) for which the improvement program was undertaken. Therefore, this method provides the plant breeder with a high degree of genetic control of his work.

The backcross method is scientifically exact because the morphological and agricultural features of the improved variety could be described in advance and because the same variety could, if it were desired, be bred a second time by retracing the same steps (Briggs, "Breeding wheats resistant to bunt by the backcross method," *Jour. Amer. Soc. Agron.*, 22:289-244 (1930)).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be modified only with regards to genes being transferred, which are maintained in the population by selection.

Successful backcrosses are, for example, the transfer of stem rust resistance from 'Hope' wheat to 'Bart' wheat and even pursuing the backcrosses with the transfer of bunt resistance to create 'Bart 38', having both resistances. Also highlighted by Allard is the successful transfer of mildew, leaf spot and wilt resistances in 'California Common' alfalfa to create 'Caliverde'. This new 'Caliverde' variety produced through the backcross process is indistinguishable from 'California Common' except for its resistance to the three named diseases.

One of the advantages of the backcross method is that the breeding program can be carried out in almost every environment that will allow the development of the character being transferred.

The backcross technique is not only desirable when breeding for disease resistance but also for the adjustment of morphological characters, color characteristics, and simply inherited quantitative characters, such as earliness, plant height, and seed size and shape. In this regard, a medium grain type variety, 'Calady', has been produced by Jones and Davis. As dealing with quantitative characteristics, they selected the donor parent with the view of sacrificing some of the intensity of the character for which it was chosen, i.e., grain size. 'Lady Wright', a long grain variety was used as the donor parent and 'Coloro', a short grain variety as the recurrent parent. After four backcrosses, the medium grain type variety 'Calady' was produced.

Chicory Plants

Chicory is a multipurpose herbaceous plant whose adult green leaves are often cultivated for salads, chicons (blanched buds), or for roots which can be baked and ground for use as a coffee substitute. Chicory is sometimes also grown as a forage crop for livestock. Chicory is native to Europe, and North America.

Common chicory is also known as blue daisy, blue dandelion, blue sailors, blue weed, bunk, coffeeweed, among other names. Its green leaves are often considered to be bitter, and are used in some European cuisines. The leaves can also be blanched to reduce bitterness for incorporation into other dishes.

Witloof ("white leaf") chicory type varieties are grown under forcing conditions to produce chicons. These plants tend to be grown underground or in specially designed indoor facilities without sunlight in order to prevent the leaves from turning green or opening up. The resulting crop resembles etiolated buds of pale color. Because of the phenotypic requirements of this type of cultivation, chicory varieties designated for chicon production sometimes undergo additional breeding and selection for traits specific to "forcing growth" go through breeding and selection for "forcing" conditions.

Features important to chicory cultivation are mostly analyzed according to the Guidelines for the Conduct of Tests for Distinctness, Uniformity and Stability published by UPOV as document TG/173/3 and include:

Time of Flowering

Leaf of adult plants in the field, i.e. plants than have not been subjected to forcing:
- Leaf Length: the leaf length is judged by the breeder in reference to a set of known references plants: plants 'Carla' and 'Conrad' have a short leaf length, while plants 'Elsa', 'Flash' and 'Marriott' have a medium leaf length, 'Turbo' has a long leaf length and 'Vilmorin No 5' has a very long leaf length.
- Color: the leaf color could be only green, only red or green and red.
- Intensity of green color: when the color of the leaf is green, it can be light green as in 'Jaz' plant, medium green as in 'Bea' or 'Toner' plants or dark as in 'Conrad', 'Magic' or 'Zoom' plants
- Anthocyanin on leaf blade: the anthocyanin on the leaf blade could be present or absent.
- Foliage attitude: the foliage attitude could be erect such as in 'Dirv' plant, semi erect as in 'Flash' or 'Turbo' or horizontal, such as for in the plant of the present invention 'Bobine'
- Male sterility: the male sterility could be present or absent.

Figure 3:
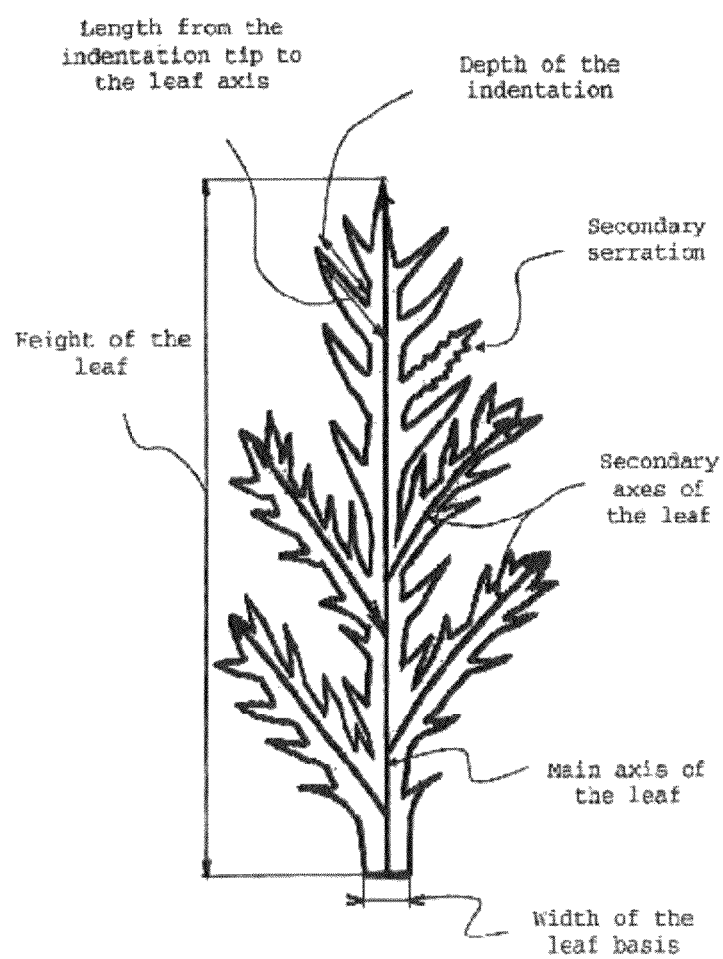
FIG. 3 represents a theoretical diagram of a wilted leaf of a plant of the *Cichorium* species of the GPI phenotype of the present invention.

Head after Forcing
- Length: the head length is judged by the breeder in reference to a set of known references plants: plant 'Carla' has a very short head length, 'Mona" has a short head length, 'Bea' and 'Monitor' have a medium head length, 'Faro', 'Focus' and 'Revor' have a long head length while plant 'Normale' has a very long head length.
- Width: the head width is rate as small as for the 'Carla' plant, medium, as in 'bea' or large as for the 'Mona' endive.
- Weight: the weight is measured in grams.
- Shape in longitudinal section: the shape in longitudinal section could range from narrow elliptic to elliptic, broad elliptic or ovate.
- Leaf length: the leaf length is measured in centimeters.
- Main leaf rib width: the main leaf rib width is measured in centimeters.
- Indentations of the limbs up to the leaf axis: the measure of the indentation of the limbs to the lead axis is shown in FIG. 3. It is measured in centimeters.
- Secondary serrations: the measure of the Secondary serrations is shown in FIG. 3. It is measured in centimeters.
- Color of the nervures: the color of the nervures is present or absent.
- Forcing time: the time, in days, for the development of the head.
- Seed Color: the seeds could be white or black.
- Bolting resistance: the plant could demonstrate an absence of bolting, such as in 'Carla', a weak tendency such as in 'Bea', a medium tendency to bolt such as in 'Flash', a strong tendency such as in Quartz or a very strong tendency such as in 'Vilmorin No 5'.

Witloof chicory cultivar 'BOBINE' is a plant from *Cichorium intybus* L species adapted to forcing culture, also called endives, has superior characteristics and was developed according to the method described in US patent publication US 2006/0260001 which is hereby incorporated in its entirety.

As endive producers are seeking novel products for diversifying their offer and allowing them to offer a varied range of endives to the final consumers, the present inventors have developed a breeding method for the creation of a new witloof chicory cultivars such as 'BOBINE'.

Witloof chicory cultivar 'BOBINE' was developed from the cross between plants 17.1 and 119729-07. Both 17.1 and 119729.07 plants are proprietary varieties developed through crosses of *Cichorium endivia* L and *Cichorium intybus* L according to the method described in US publication US 2006/0260001.

EXAMPLES

Example 1

Parental Breeding and Selection

To create the 17.1 and 11929.07 parental lines, a first batch of F1 plants was created from a cross between female plants of the variety Videna of the *Cichorium intybus* L species having tuberous roots and a batch of male plants of the variety Grosse Pommant Seule of the *Cichorium endivia* L species (FIG. 1). A second batch of F1 plants was created from a cross between female plants of the variety 1089 of the *Cichorium intybus* L species having tuberous roots and a batch of male plants of the variety Grosse Pommant Seule of the *Cichorium endivia* L species.

Both F1 generation hybrid plant populations resulting from said cross-breedings were sown and grown up to a 3 leaf stage, followed by an 8 week phase of vernalization at 5° C. so as to obtain bolting ability. These F1 plants were then self-fertilized in heated greenhouses in the presence of flies that carry out the self-fertilization. The F2 seeds obtained thereof were sown in the field, for the selection of F2 generation plants that did not present any buds or roots visible alterations caused by a viral, bacterial or fungal infection, particularly by *Erwinia carotovora*, by *Sclerotinia Sclerotiorum*, or even by *Phytophtora cryptogea*. These plants then undergo a forcing culture step for 14 days at 16° C., the same temperature as for the nutrient solution.

Figure 2:
FIG. 2 is depicts the new 'BOBINE' variety developed by the methods of the present invention.

All the F2 generation recombinant young plants possessing tuberous roots were selected. The character of possession of tuberous roots was initially provided by the genome of the parent *Cichorium intybus* L. All the selected F2 generation young plants also have in common possessing indented leaves (FIGS. 2 and 3). The character of possession of indented leaves was initially provided by the genome of the parent *Cichorium endivia* L.

It was then decided to clone the plants presenting the GPI phenotype (see definitions, and FIG. 3) to regenerate buds. Such cloning of F2 plants after forcing occurs on the "NF" medium from fragments of leaf nervures that were disinfected with calcium hypochlorite.

The regenerated buds were pricked out an appropriate M4 culture medium enriched with AIA at the final concentration of 0.2 mg/l, until young plants are obtained.

After 8 weeks vernalization at 5° C., the plants were grown in a heated greenhouse. All plants, whether coming from both original crosses were grouped together so that they can cross pollinate freely in order to try to homogenize the population. The seeds resulting thereof were sown in the field where they gave plants that were selected from the phenotype standpoint by their common ability to tuberize, i.e. to develop roots adapted to forcing cultivation. This F3 generation plants were subject to a new forcing step under the same conditions as in the first forcing step, as well as, thereafter, to a new cloning step from leaf nervures for the plants presenting the GIP desired phenotype. An F4 generation was regenerated on NF specific medium, followed by a pricking step on an M4 medium for rooting.

After 8 weeks vernalization at 5° C., the plants were grown in a heated greenhouse. And individually self-pollinated. The seeds resulting thereof were sown in the filed where they did not show any deficiency, harvested for a forcing step where they showed a good forcing ability as well as the desired GPI phenotypic characteristics.

Example 2

Breeding and Selection of 'BOBINE' Variety

Both plants 17.1 and 119729.07 used in the creation of the 'BOBINE' cultivar are derived from the previously obtained plants having the GPI phenotype, 17.1 having a yellow limb while 119729.07 has a red limb.

In a first step, plants 17.1 and 119729.07 were crossed to generate F1 plants. In order to increase the number of plants available to choose for the best phenotype selection, the F1 plants were self-pollinated to create F2 plants. About 1000 plants were obtained and forced, among which only 15 presented the phenotypic characteristics that the breeder was looking for after forcing, including yellow limb and very high indentations. The selected plants were self-pollinated and again, in the population obtained and submitted to the forcing culture, only 6 plants were selected based on the yellow limb and numerous and deep indentations. These 6 plants were self-pollinated to obtain F4 plants that were considered sufficiently homogeneous. The plants were cloned in order to increase their number and the 200 plants obtained thereby were cross pollinated during two generations to fully homogenize the population that is now known as the variety 'BOBINE'.

Cultivar 'BOBINE' is a witloof chicory due to its capability of producing heads under forcing culture conditions. The indentations of its leaves make it however unique in regard to all other endive varieties that are not known to present any such indentation. FIG. 2 shows an exemplary 'BOBINE' chicon grown under forcing cultures. The 'BOBINE' variety is novel over other chicons such as the one shown in FIG. 1.

The new witloof chicory 'BOBINE' has shown uniformity and stability for the traits, as described in the following Variety Description Information. The cultivar has been increased with continued observation for uniformity. No variant traits have been observed or are expected for agronomically important traits in witloof chicory cultivar 'BOBINE'.

Example 3

'BOBINE' Morphology

Witloof chicory cultivar 'BOBINE' has the following morphologic and other characteristics (based primarily on data collected at Limagrain station, 62182 Villers Les Cagnicourts, France, for the cultivation step and Vilmorin breeding station, 49250 La Ménitrè, France for the forcing steps, all experiments done under the direct supervision of the applicant). See Table 1 for a summary of measured characteristics.

TABLE 1

Chicory Morphologies.

| Morphology | 'Ecrine' | Parent 17.1 | Parent 119729.07 | 'BOBINE' |
|---|---|---|---|---|
| Adult Plants Under Field Conditions | | | | |
| Time of Flowering | Medium | NA | NA | Early |
| Leaf Length | Short | Short | Long | Short |
| Leaf Color | Only green | Only Green | NA | Only Green |
| Leaf Color Intensity | Light green | NA | NA | Light green |
| Anthocyanin on Leaf Blade | Absent | Absent | Present | Absent |
| Foliage Attitude | Erect | Erect | Horizontal | Horizontal |
| Male Sterility | None | None | None | Absent |
| Seed Color | White | White | White | White |
| Bolting Resistance | Strong | NA | NA | Medium |
| Plants Grown Under Forcing Conditions | | | | |
| Length | Medium | Short | Long | Medium |
| Width | Large | NA | NA | Medium |
| Weight | More than 200 g | NA | NA | About 100 g |
| Shape in Longitudinal Sections | Narrow Elliptic | NA | NA | Narrow Elliptic |
| # of Leaves | 30 | NA | NA | 30 |
| Leaf Length | 16 | NA | NA | 18 cm |
| Main Leaf Rib Width | 6 | NA | NA | 2 cm |

TABLE 1-continued

Chicory Morphologies.

| Morphology | 'Ecrine' | Parent 17.1 | Parent 119729.07 | 'BOBINE' |
|---|---|---|---|---|
| Indentations of the Limbs of Leaves Length | 0 | NA | NA | 3.5 cm |
| Indentations of the Limbs of Leaves Number | 0 | NA | NA | 24 average/leaf |
| Ratio Depth of the Indentation/Length of the indentation | 0 | NA | NA | .90 |
| Secondary Serrations | 0 | NA | NA | 2.5 mm |
| Color of the nervures | Absent | NA | NA | Absent |
| Color of the Limb | Yellow | NA | NA | Yellow |
| Forcing Time | 21 Days | NA | NA | 21 Days |

The 'BOBINE' variety of the present invention is novel over other *Cichorium intybus* L varieties currently available. Table 1 compares the morphologies of the new 'BOBINE' variety of the present invention, to that of its closest comparable variety 'Ecrine'. The new 'BOBINE' variety shares many qualities with variety 'Ecrine', but differs from 'Ecrine' both under field conditions where the foliage attitude of 'BOBINE' is horizontal while 'Ecrine' is erect, and under forcing conditions where the length of the head is longer for 'BOBINE'. One of the most striking differences is that 'BOBINE' has indentations of the limbs of its leaves during forcing culture, while 'Ecrine' does not have such indentations (for a representative picture of a traditional endive compared to the new 'BOBINE' endive, compare FIGS. 1 and 2). Forcing data for parental varieties 17.1 and 119729.07 is not included in Table 1 because forcing culture is traditionally performed on hybrid plants. Thus a comparison of the BOBINE hybrid variety of the present invention to the inbred parental lines would not make sense from a grower's perspective.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the non-limiting exemplary methods and materials are described herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Nothing herein is to be construed as an admission that the present invention is not entitled to antedate such publication by virtue of prior invention.

The disclosures, including the claims, figures and/or drawings, of each and every patent, patent application, and publication cited herein are hereby incorporated herein by reference in their entireties.

The following description includes information that may be useful in understanding the present invention. It is not an admission that any of the information provided herein is prior art or relevant to the presently claimed inventions, or that any publication specifically or implicitly referenced is prior art.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

DEPOSIT INFORMATION

A deposit of the witloof chicory seed of this invention is maintained by Vilmorin, La Ménitré, Station de Recherche, Route du Manoir, 49250 La Ménitré, France. In addition, a sample of the witloof chicory seed of this invention has will be deposited with the National Collections of Industrial, Food and Marine Bacteria (NCIMB), 23 St Machar Drive, Aberdeen, Scotland. AB24 3RY, United Kingdom.

To satisfy the enablement requirements of 35 U.S.C. 112, and to certify that the deposit of the isolated strain of the present invention meets the criteria set forth in 37 CFR 1.801-1.809, Applicants hereby make the following statements regarding the deposited witloof chicory cultivar 'BOBINE' (deposited as NCIMB Accession No. 42468):

1. During the pendency of this application, access to the invention will be afforded to the Commissioner upon request;
2. Upon granting of the patent the strain will be available to the public under conditions specified in 37 CFR 1.808;
3. The deposit will be maintained in a public repository for a period of 30 years or 5 years after the last request or for the enforceable life of the patent, whichever is longer; and
4. The viability of the biological material at the time of deposit will be tested; and
5. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the NCIMB.

The invention will be irrevocably and without restriction released to the public upon the issuance of a patent.

What is claimed is:

1. A seed of witloof chicory cultivar designated 'BOBINE', wherein a representative sample of seed of said cultivar has been deposited under NCIMB No. 42468.

2. A witloof chicory plant, or a part thereof, produced by growing the seed of claim 1.

3. A witloof chicory plant, or a part thereof, having all the physiological and morphological characteristics of witloof chicory cultivar 'BOBINE' listed in Table 1.

4. A witloof chicory plant, or a part thereof, having all the physiological and morphological characteristics of witloof chicory cultivar 'BOBINE' listed in Table 1, wherein a representative sample of seed of said cultivar is the seed of claim 1.

5. A tissue culture of regenerable cells produced from the plant of claim 2 wherein said cells of the tissue culture are produced from a plant part selected from the group consisting of embryos, meristematic cells, leaves, pollen, root, root tips, stems, anther, pistils, flowers, and seeds.

6. A witloof chicory plant regenerated from the tissue culture of claim 5, said plant having all the morphological and physiological characteristics of witloof chicory cultivar 'BOBINE' listed in Table 1, wherein a representative sample of seed has been deposited under NCIMB No. 42468.

7. A method for producing a witloof chicory seed comprising crossing a first parent witloof chicory plant with a second parent witloof chicory plant and harvesting the resultant hybrid witloof chicory seed, wherein said first parent witloof chicory plant or second parent witloof chicory plant is the witloof chicory plant of claim 2.

8. A hybrid witloof chicory seed produced by the method of claim 7.

9. A method of introducing a desired trait into witloof chicory cultivar 'BOBINE' comprising:

(a) crossing a witloof chicory cultivar 'BOBINE' plant grown from witloof chicory cultivar 'BOBINE' seed, wherein a representative sample of seed has been deposited under NCIMB No. 12468 with another witloof chicory plant that comprises a desired trait to produce $F_1$ progeny plants, wherein the desired trait is selected from the group consisting of insect resistance, disease resistance, water stress tolerance, heat stress tolerance, improved shelf life, delayed shelf life, increased leaf number and male sterility;

(b) selecting one or more progeny plants that have the desired trait to produce selected progeny plants;

(c) crossing the selected progeny plants with the witloof chicory cultivar 'BOBINE' plants to produce backcross progeny plants;

(d) selecting for backcross progeny plants that have the desired trait and physiological and morphological characteristics of witloof chicory cultivar 'BOBINE' listed in Table 1 to produce selected backcross progeny plants; and (e) repeating steps (c) and (d) three or more times in succession to produce selected fourth or higher backcross progeny plants that comprise the desired trait and the physiological and morphological characteristics of witloof chicory cultivar 'BOBINE' listed in Table 1.

10. A witloof chicory plant produced by the method of claim 9, wherein the plant has the desired trait and all the physiological and morphological characteristics of witloof chicory cultivar 'BOBINE' listed in Table 1.

11. A method for producing witloof chicory cultivar 'BOBINE' seed comprising crossing a first parent witloof chicory plant with a second parent witloof chicory plant and harvesting the resultant witloof chicory seed, wherein both said first and second witloof chicory plants are the witloof chicory plant of claim 4.

12. A witloof chicory head, produced by forcing the plant of claim 2.

* * * * *